(12) United States Patent
Cherfas et al.

(10) Patent No.: US 7,300,442 B2
(45) Date of Patent: *Nov. 27, 2007

(54) METHOD OF DESTROYING FORMATIONS IN A BODY

(76) Inventors: Daniel Cherfas, 286 Corbin Pl. #5B, Brooklyn, NY (US) 11235; Marika Cherfas, 286 Corbin Pl. #5B, Brooklyn, NY (US) 11235

( * ) Notice: Subject to any disclaimer, the term of this patent is extended or adjusted under 35 U.S.C. 154(b) by 834 days.

This patent is subject to a terminal disclaimer.

(21) Appl. No.: 10/667,880

(22) Filed: Sep. 22, 2003

(65) Prior Publication Data

US 2004/0059342 A1    Mar. 25, 2004

Related U.S. Application Data

(63) Continuation-in-part of application No. 09/902,007, filed on Jul. 11, 2001, now Pat. No. 6,623,489.

(51) Int. Cl.
*A61D 1/12*    (2006.01)

(52) U.S. Cl. ...................... 606/106; 128/898

(58) Field of Classification Search ............... 606/106, 606/159, 205, 207, 210, 211; 128/898
See application file for complete search history.

(56) References Cited

U.S. PATENT DOCUMENTS

| 5,782,834 | A * | 7/1998 | Lucey et al. ............... 606/22 |
| 6,398,798 | B2 * | 6/2002 | Selmon et al. ............. 606/159 |
| 6,623,489 | B2 * | 9/2003 | Cherfas et al. ............ 606/106 |

* cited by examiner

*Primary Examiner*—Michael J. Hayes
*Assistant Examiner*—Victor X. Nguyen
(74) *Attorney, Agent, or Firm*—I. Zborovsky

(57) ABSTRACT

A method of destroying formation in a body includes introducing a tubular member into a body to an area of a formation with a gripping unit movable between an open position and a closed position in which the gripping unit encloses a closed space to confine the formation inside the closed space, destroying the formation by a formation destroying element and withdrawing a device from a body with the formation and its fragments confined inside the closed space formed by the gripping unit in its closed position.

10 Claims, 5 Drawing Sheets

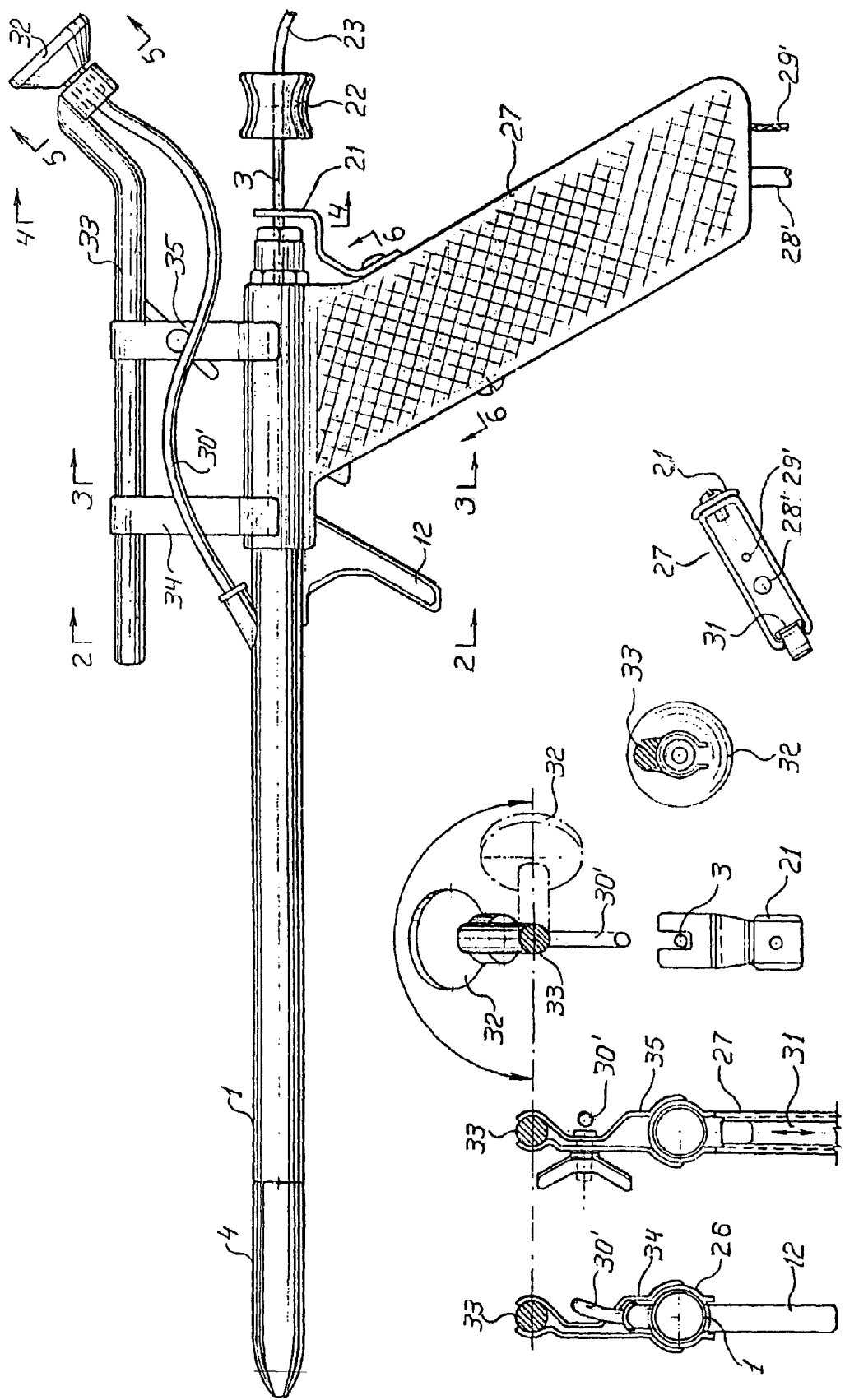

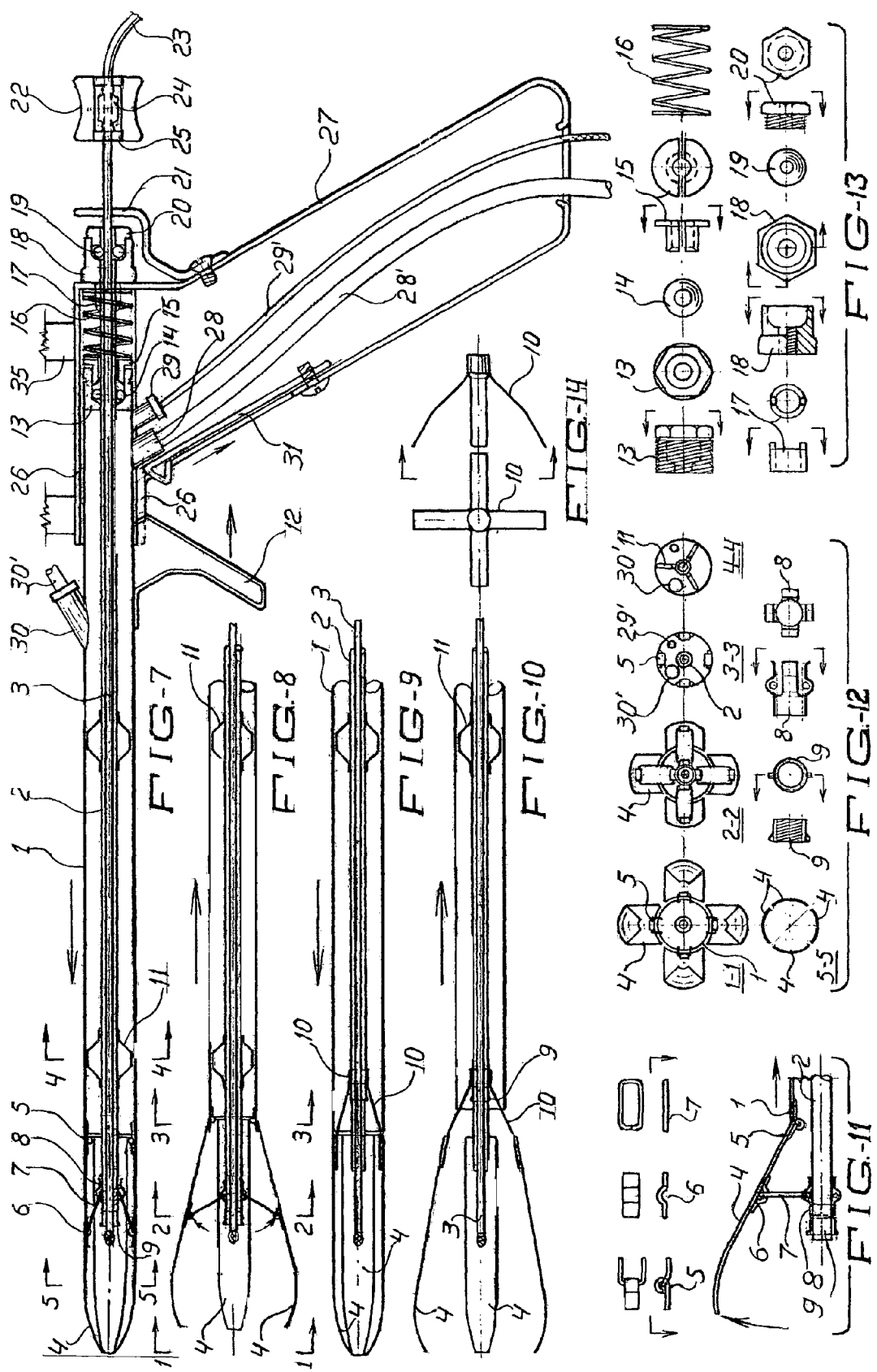

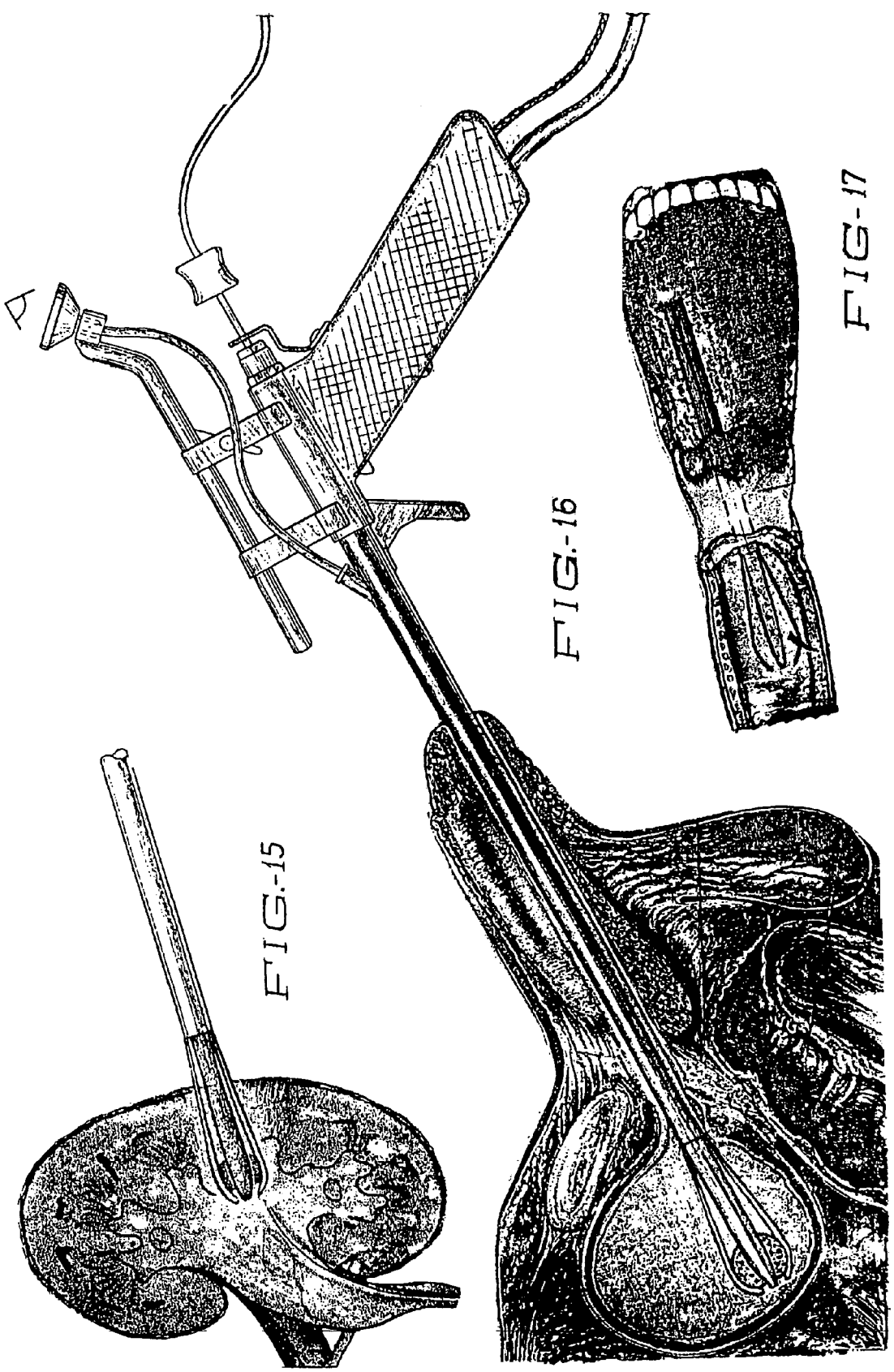

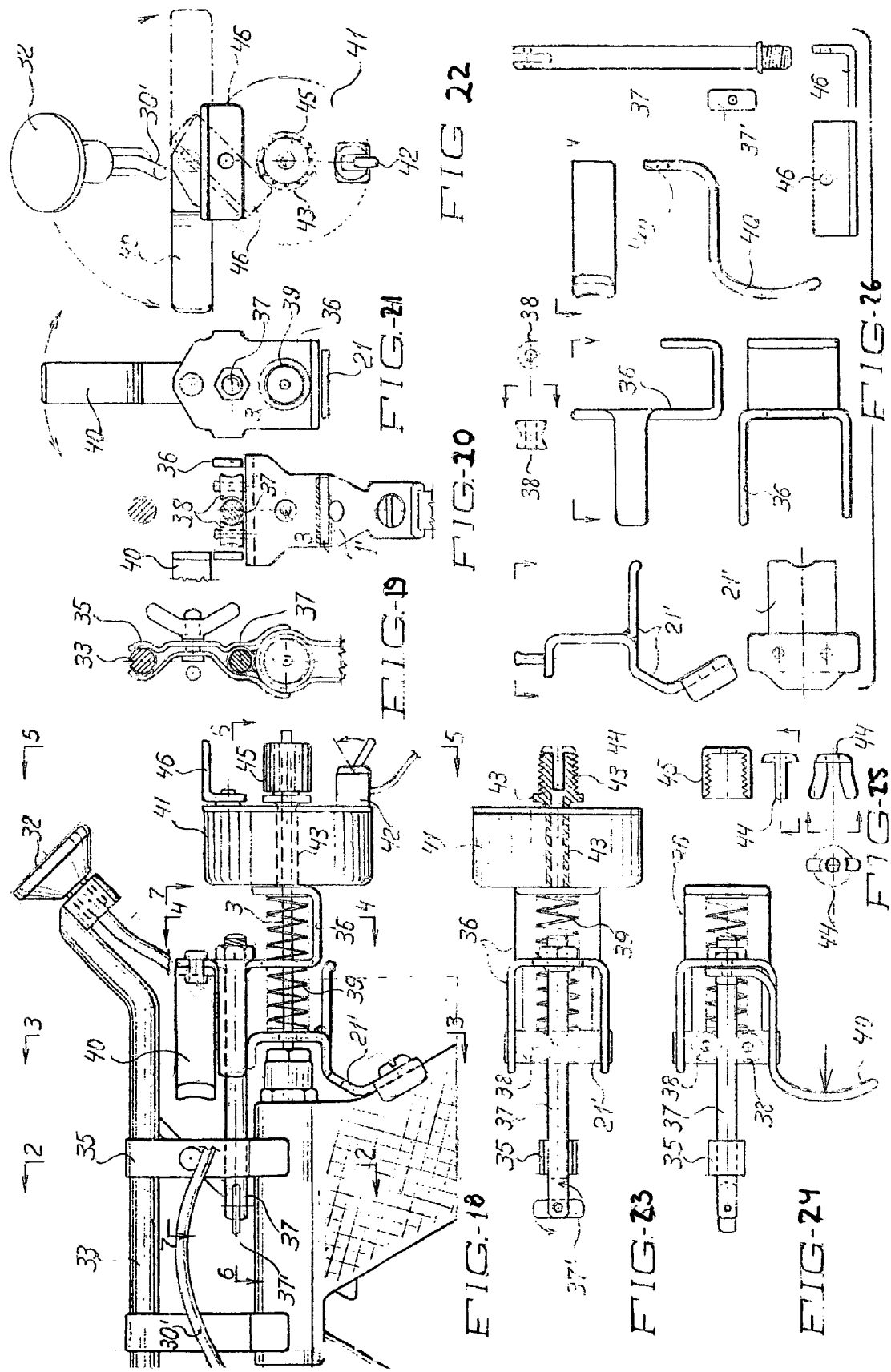

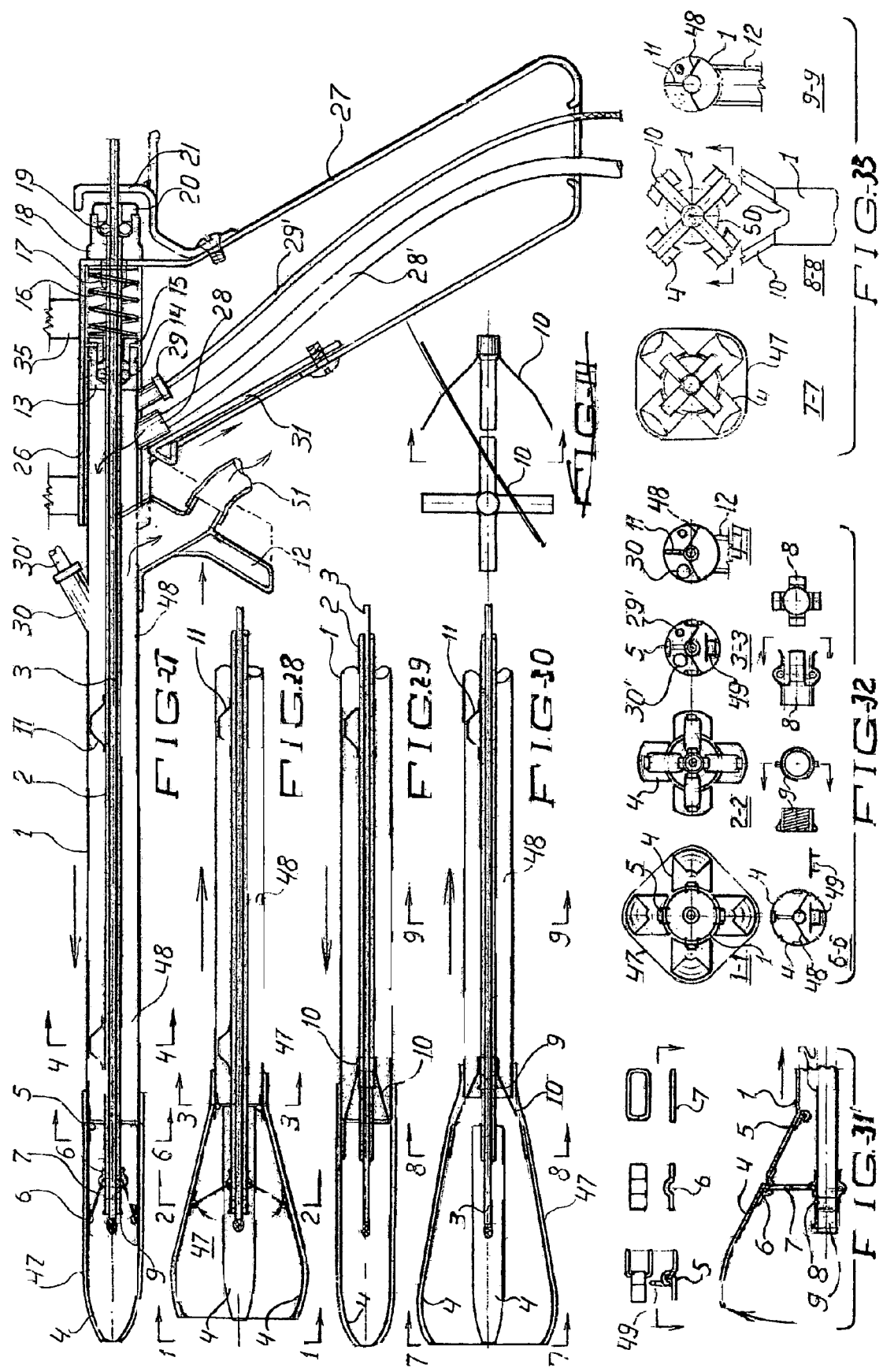

METHOD OF DESTROYING FORMATIONS IN A BODY

CROSS-REFERENCE TO A RELATED APPLICATION

This application is a continuation-in-part of application Ser. No. 09/902,007 filed on Jul. 11, 2001 now U.S. Pat. No. 6,623,489.

BACKGROUND OF THE INVENTION

The present invention relates to a method of destroying formations in a body, in particular in internal organs, in deep wounds and other areas which are difficult to access, without surgical operations, with minimal trauma, so that corresponding formations can be destroyed and if necessary extracted from the body. Further methods are disclosed for example in U.S. patent to Nash U.S. Pat. No. 4,811,735 and Heidmueller U.S. Pat. No. 5,281,230. Foreign formation can include stones, growths, bullets logged in wounds, food stuck during eating, etc.

Methods of destroying corresponding formations in the body are known. Some of them include surgical methods, in accordance with which a corresponding organ is made accessible by a surgical operation, and the formation is destroyed and/or removed. Other methods include for example ultrasound crashing of stones, etc. It is believed that existing methods and devices can be further improved.

SUMMARY OF THE INVENTION

Accordingly, it is an object of the present invention to provide method of destroying foreign formations in a body.

In keeping with these objects and with others which will become apparent hereinafter, one feature of present invention resides, briefly stated, in a method of destroying foreign or undesirable formations in a body which includes introducing a tubular member into a body to an area of a formation with gripping means provided at a front end of the tubular member and having a plurality of gripping elements which are movable between an open position in which said gripping elements are spaced from one another around an axis of the tubular member and a closed position in which said gripping elements laterally abut against one another without gaps therebetween to enclose a substantially closed space; moving the tubular member axially in a first axial direction so that the griping elements connected to the tubular member are displaced to their open position to surround a formation; destroying the formation by a formation destroying element which is introduced through an interior of the tubular member with a working head brought in contact with the formation and rotatable to destroy the formation; moving the tubular member in an opposite direction so as to move the gripping elements to their closed position to confine fragments of the formation in the closed space; withdrawing the tubular member from the body with the fragments confined inside the closed space formed by the gripping elements in their closed position.

When the method is performed in accordance with the present invention, it makes possible a destruction and if necessary withdrawal of formations from the body in a simple, efficient, and non intrusive way.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a general view of a device which uses a new method for destroying foreign formations in a body;

FIGS. 2, 3, 4, 5 and 6 are views showing a cross-section of the device shown in FIG. 1 taken along the lines 2-2, 3-3, 4-4, 5-5 and 6-6 correspondingly;

FIG. 7 is a view substantially corresponding to the view of FIG. 1 but showing a longitudinal cross-section of the device which uses a new method in accordance with the present invention;

FIG. 8 is a view showing one embodiment of the device of FIG. 1;

FIGS. 9 and 10 are views showing another embodiment of the device in accordance with the present invention in a closed and an open position correspondingly;

FIGS. 11 and 12 are views showing details of the inventive device of the embodiment of FIG. 8 in a front area;

FIGS. 13 is a view showing details of a rear area of the device which uses the inventive method;

FIG. 14 is a view showing a working head part of the device which uses the inventive method;

FIGS. 15, 16, and 17 are views showing the device which uses the inventive method used for destruction of formations in a kidney, in a male bladder and in a food pipe correspondingly;

FIGS. 18-26 are views illustrating a method with the use of the device shown in the preceding figures together with an additional attachment which provides additional comfort during the use of the device; and FIGS. 27-32 are views substantially corresponding to the views of FIGS. 7-12 but showing an additional embodiment of the inventive method with the modification of the device for use in the method; and FIG. 33 is an additional drawing showing a fragment of the device.

DESCRIPTION OF THE PREFERRED EMBODIMENTS

A method of for destroying and/or extracting foreign formations in a body includes introduction of a tubular member which is identified as a whole with reference numeral 1. A tube 2 of a smaller diameter is located in the tubular member 1, and a rod 3 extends through an interior hollow of the tube 2. The rod 3 is a rigid shaft which has a front end provided with a working head, such as for example a drill, a bit, and the like. The opposite end of the rod 3 extends outwardly from the tubular member to be connected with a flexible shaft 23. The front, head part of the tubular member ends in cigar-shaped and composed of petal-shaped tongues 4. The tongues 4 have bent ends which form grippers when they are open.

In accordance with one embodiment of the present invention which involves the use of a hinges, each tongue is provided at its base with a hinge 5 for turning. The hinge 5 includes a plate which is bent from one side and in which a hook is introduced. The plate is soldered to the tongue and the hook is soldered to the inner surface of the end of the tubular member 1 as shown in FIGS. 7, 8, 11, 12. In order to control the turning, a hinge 6 is soldered or welded to an inner surface of each tongue at a distance from its axis of turning. The hinge 6 includes a bent plate 6 with a frame 7 in it. The central element of the hinge unit is a casing 8 which is composed of a spring, alloyed steel. Bent legs of the casing embrace the tube 2 from all sides. During mounting, second ends of the frames 7 are introduced into the hooks. The casing 8 is placed on the tube 2 and fixed from one side by a soldered abutments and from another side by a bush 9 which is screwed on the end of the pipe 2. In order to turn the bush, two abutments are soldered on its outer surface.

In accordance with another embodiment of the present invention, a gripper 10 composed for example of spring, alloyed steel, is arranged on the end of the pipe 2. The gripper which is fixed by the soldered abutments on the pipe 2 from one side is also locked by screwing of the bush 9 on the end of the pipe 2. Sliders 11 are soldered on the pipe 2 and form inner supports which fix the central position of the pipe 2 in the tubular member 1.

The rear end of the tubular member is shown in FIGS. 7 and 13. In order to provide hermetization of the tubular member a special bushing 13 is screwed into its rear part from outside. The bushing has a cavity, through which the pipe 2 extends. For hermetization of the pipe 2, a sealing ring 14 is arranged on it inside the bushing. Then halves of an insert 15 which is separated into halves is introduced into the interior of the bushing 2. The outer ends of the halves of the insert are supported on the inner side of the bushing and take a pressure from a spring 16. Furthermore, for fixing the tube 2 from a longitudinal and turning movement, a special bush 17 is placed on it and located in a chamber of the spring. The left side of the bush is soldered to the pipe 2. The right side of the bush is formed with two thorns which during mounting are inserted into the drilled openings in the rear wall of the upper part of the device. A special bushing 18 is screwed on the end of the pipe 2 which extends beyond the rear wall, and is tightened. The rigid shaft 13 extends through the bushing. For the hermetization in the bushing, a sealing ring 19 is provided. The interior of the bushing 18 is closed by a plug 20 which is screwed into it and the shaft 3 freely extends through the plug. The shaft 3 extends through a limiting member 21 which is screwed to the upper part of a handle of the device.

A control handle 22 formed as a coil is arranged at the outside, rear side of the device at a certain distance. An end of the rigid shaft 3 extends from the left side into the handle, while the end of the flexible shaft 23 which extends from a rotary drive is introduced from the right end. The ends of both shafts are arranged in known rolling or sliding bearings 25. Furthermore, the ends of both shafts are introduced into a connecting coupling 24. After the connection a coil 22 is placed on the bearings and the coupling 24. After this, both outside races of the bearings are fixed in the coil.

The rear end of the tubular member and the spring are located in a cylindrical element 26 which embraces them but is open in the lower part. At the front, the open part of the cylindrical member has bend parts, in which an upper part of a cock 12 can move. The rear part of the open end of the cylindrical member transits into a hollow handle of the device 27. Two nipples 28 are soldered into the lower part of the tubular member. They are used for connection of a hose 28' for supply a cleaning medium, for example water. A nipple 29 is used for introducing an electric cable 29' for power supply to an illuminating bulb at the end of a light guide 30'. The hose and the electrical cable are extended from the device through a lower part of the handle so as not to interfere with one another and lead to a power source.

A window which is closed by a special cover 31 is located in the upper front part of the device handle. The cover has a triple function. From the outer side, its upper bend is a limiting member for the cock 12 when it is moved rearwardly. From the inner side, the upper part of the cover blocks the spring-biased tubular member and is a support for the nipple 28 in the tubular member. For disassembly of the device, the clamping screw is released and the cover is lowered so that the tubular member with the nipples can be removed and withdrawn from the window in the handle (hose 28' and cable 29').

The device can have a support for an eyepiece 32 and a light guide 30' which extends from the eyepiece and has a known construction. The light guide is inserted into the tubular member through a nipple 30. The eyepiece is arranged on a standing part of a member 33. The member 33 is movable and can move forwardly and rearwardly and turn to the left and right due to its circular cross-section. This member is arranged on two supports 34 and 35 which are soldered to the casing 26. The support 35 has a tightening nut for fixing the member with the eyepiece at any lower position.

The central rod 3 or the shaft can have any length. It can be exchangeable. It can have a head with any working elements, attachments, etc.

The method is performed in the following manner.

A medical practitioner holds the device by taking its handle with all fingers of left or right hand. The tubular element is introduced into an interior organ or cavity of a patient. With monitoring of the movement of the tubular member on a screen or an X-ray device, the working head of the rod 3 is introduced through the tubular element to a formation, for example a stone which has to be removed. With the pointing finger the practitioner pulls the cock 12, the cock presses the spring 16, so that the tubular member is moved rearwardly a few millimeters. In the embodiment with the hinge, the tubular element moves the tongues 4, the tongues 4 pull the frames 7 in which they are hingedly connected to them, and the frames 7 which have a hinged, immovable support on the tube 2 turn to the sides and move tongues outwardly. In the gripper embodiment, the gripper moves rearwardly and releases the spring biased elements of the gripper and they turn the tongues 4, so that the spaced tongues form gripping elements. The tubular element is moved forwardly, and the tongues are placed on the formation, for example on a stone. The cock is then released forwardly, and the tubular member moved forwardly. In the hinged embodiment, the tongues which are pushed by the tubular element turn the frames 7, and the latter are turned in the hinges of the casing 8 so as to press the tongues to the center. In the gripper embodiment, the gripping tongues which are pushed by the tubular member also will press the tongues to the center so as to form gripping members which block the stone.

Then a not shown rotary drive is energized, and the rigid drill shaft 3 is rotated together with the working head formed for example as a tool. The practitioner looks into the eyepiece and sees the stone. By displacement of the coil 22 forwardly, the practitioner introduces the drill into the stone and causes its destruction. The removal of the destroyed stone does not cause any problem.

When the method is utilized in therapeutic purposes, the end of the shaft 23 can be provided with special attachments which are located in the front area of the tubular element when it is introduced into an organ. Then the front part is opened and the shaft of the attachment is moved forwardly for treatment of corresponding problems or for administration of medications. The head of the light guide can be also moved forwardly. For this purpose, the sealing cover is released on the nipple 30 and the light guide is moved and lengthened.

With the inventive method it is possible to spread tissues in order to perform examination and touch an object which has to be destroyed, removed or treated. It is possible to destroy and remove foreign formations in internal organs, such as stones and growths of any size. It is possible to withdraw from a body foreign objects which accidently were introduced into the body. It is also possible to provide local therapeutic treatment in the interior organs, by administering corresponding medications.

As explained herein above the tongues 4 are formed as petal-shaped tongues. As shown in FIGS. 1, 7 and 12, in the non-operative position the tongues 4 abut against one another in a lateral direction so that there are no lateral gaps therebetween (or have smallest possible gap therebetween), as shown in section 5-5 on FIG. 12. This feature is exceptionally important for the present invention. When the tubular member 1 is introduced into a cavity in the body, the tongues 4 are opened, and a formation which is gripped by the tongues is broken, the tongues 4 then can be displaced in their closed position, the pieces of the formation can be confined completely in the substantially closed space formed by the tongues or the gripping elements, so that the pieces or fragments are completely withdrawn from the body and can not be lost inside the body. Also, it is possible to introduce medications into inner cavities of the body, in which case also the tongues 4 are in their closed positions with no gaps therebetween, so as to deliver the medication into the corresponding cavity and then they are moved to their open positions so to release the medication in the corresponding cavity. Also, pathological formations can be stripped, removed, or cut from walls of inner cavities by moving the tongues 4 from their open position to their closed positions, so that the side edges of the tongues 4 perform the cutting action.

In the closed positions the tongues 4 laterally abut against one another so that there are no side gaps between them. While in FIG. 1 the front end of the tubular member 1 with the tongues 4 in their closed position has a small opening, the tongues 4 can be formed so that there is no front opening at all as shown in FIG. 7a. Thus, the space enclosed by the tongues 4 is completely closed both laterally and from the front end.

An additional attachment is shown in FIGS. 18-26 to be used in the inventive method. It has an element 21 which is mountable on the handle instead of the removable element. On a bent portion of a vertical wall of the element 21, a movable part of the attachment is installed. In order to perform a straight movement, a guiding cylindrical rod is arranged on the vertical wall of an element 36. The rod is fixed at the bottom by a nut. The straight movement of the rod 37 is provided by two supports which surround it. The front part of the rod 37 slides in a lower clearance of a support 35. The rear part of the rod 37 rolls in rollers 38. The rollers are located on spindles which are mounted on the bent portion of the element 21', as shown in FIGS. 18, 21, 23 and 26.

In order to provide securing from falling out of the movable part of the attachment, the end of the rod 37 has a turnable stop 37'. For axial stability of the movement of the movable part of the vertical wall of the element 36, two consoles are bent forwardly, as shown in FIGS. 18, 23 and 26. The consoles are supported and slide during the movement along the portion of the element 21' at both sides of the rollers 38. Through the round hole in the lower part of the front wall of the elements 36, the central rod 3 is passed as well as a return spring 39. The spring is mounted in a rear wall of the element 36 and abuts at the opposite side against the vertical wall of the element 21'. A member 40 is movably arranged in the upper part of the front wall of the element 26, above the rod 37. The member 40 can be turned in a vertical plane over 180° and assume a left position or a right position. The arch-shaped bend of the member 40 is provided for abutment of thumb of right or left hands.

An electric motor 41 is arranged on the rear wall of the element 36. It is supplied from an outside source or from a battery in the handle. A switch 42 can be arranged on the housing of the electric motor. A rotor is arranged on the shaft of the electric motor 43, which has a throughgoing opening for the rod 30 and passes from the rear end of the electric motor so as to form a projection. The projection is used for placement of a clamping device for the rod 3. In addition, a disc having a frictional surface is arranged there. The clamping device includes an insert 44 arranged in the shaft 43 and having two projections and made for example from TEFLON, as shown in FIGS. 23 and 25.

A cap 45 having an inner thread with rounded tips engages with the outer thread. When screwing, the thread of the cap 45 presses the projections so that they are introduced into the middle and pressed against the rod 3, so as to fix the rod and to make it turn together with the shaft 43. In order to screw off and screw on of the cap 45, the shaft 43 has to be braked, which can be done by an angle 43. The angle provides an upper protection of the shaft and has a lower rib with the frictional surface. When it is necessary to fix the shaft 43 from rotation, the angle 46 is turned and pressed against the disc of the shaft 43 as shown in FIGS. 23, 22, 25, 26.

In order to mount the attachment, the element 21 has to be removed and the element 21 is installed. The stop 37' on the element 37 is turned to an initial position. The member 40 is turned to the left or to the right depending on the use of the right or left hand. The rod 3 is passed through the spring 39 and through the shaft 43 outwardly. The rod 37 is introduced through the roller 38 and then into a clearance of the support 35 and the stop 37' is turned. The insert 44 is introduced into the clamping device, the angle 46 is lowered and pressed to the disc 43, and then the cap 45 is fitted on and turned to the end.

In the inventive method with the use of the above mentioned attachment, after the device is introduced into a cavity for treating an organ of a patient, the head is placed close to a pathological formation to be destroyed and removed. The cock 12 is pressed so as to open the head of the device and to surround the formation. In order to destroy the formation the electric motor 41 is turned on, and the rod 3 with the attachment is rotated. By pressing the member 40, the movable part of the attachment is moved straight, so that the rod 3 introduces the attachment into the formation and breaks it. Then a physician removes pressure of a thumb from the member 40 and the spring 39 returns the rod 3 with the attachment to an initial position. The second hand of the physician is free for other actions.

When it is necessary to destroy large rigid stones the fragments can fly out through clearances between the tongs 4 which are not completely closed. For this case it is proposed to put a special cap, which can be composed of a thin medical rubber. The cap 47 does not prevent opening of the tongs 4 and at the same time it limits a space in which the destruction of stones can be performed, as shown in FIGS. 27-33.

After the destruction of stones, in order to remove small fragments and other dirt cleaning and washing of the cavity of an organ can be performed with the use of the inventive method. For this purpose the device can be retained in the cavity, and just used for cleaning or removal.

In order to do this the device is provided with two longitudinal passages, formed for example by two longitudinal strips 48 which are soldered to the tube 2 at an angle of 120°. The strips also perform the functions of a slider as shown in the drawings. The upper passage is used for communications and water supply which is supplied from an elastic pipe 28. The lower passage serves for water which is withdrawn from the cavity of an organ together with fragments of destroyed stones and other dirt.

An element 49 formed as a trapeze is soldered to the element 5 for protection of the lower passage from its blocking with large fragments, as shown in FIGS. 31 and 32. The other end of the lower passage reaches the hollow cock, and is connected with it through an opening. In order to remove the cock from the cavity, it has an outlet pipe at the rear side. An elastic hose 51 is connected with the outlet pipe. The outlet pipe and the hose is placed due to the free space located behind the cock. Then the hose is moved to the left or to the right, as convenient for the use.

When the tubular element has tong, the passage of water into the lower passage depends on a width of the tong portions. If the passage is loaded, it is not necessary to install the element 49. For a greater opening of the passage a cutout 50 can be provided in the lower edge of the passage between the tongs as shown in FIG. 33.

In order to turn on a cleaning process, faucets are opened on the hose 28 and 51. Water which is supplied under pressure in the pipe 28' flows into the upper passage and from there into a cavity to be washed. When the water reaches a sufficient pressure the water from the cavity flows with the dirt to the open lower passage. From the lower passage it flows through the hollow of the cock 22 and the hose 51 outwradly.

By movement of the cock, the user can cause pulsation in the zone of grippers, and also causes movement of the element 49 and the bottom of the lower passage. This enhances movement of water with dirt outside.

In the present time during operations of adenomectomoy (surgical removal of adenoma through a bladder), tamponage of bladder can develop with extensive bleeding into a cavity. Solidified mass of blood is formed in the bladder and a surgical opening of the bladder must be performed. The method in accordance with the present invention can provide treatment without a surgical opening of the bladder. For this purpose the above mentioned rubber cap is placed on the device and has an opening in its front part which can be open. When it is open inside the bladder, an expanded mouth for taking and sucking out of the solidified mass of blood is formed. The mouth has therefore a rubberized outer surface and does not traumatize the inner mucus surface of the bladder. In order to remove the mass from the bladder a vacuum can be utilized. For this purpose the hose 51 connected to the cock 12 is connected with a vacuum extractor.

Also, nowadays when cancerous tumor is found on a mucus surface of the bladder, a surgical procedure is utilized with a subsequent chemo- and radio- therapy. With the inventive method this is no longer necessary. In the inventive method the device with the rubber cap allows to surround the cancerous tumors, a portion of the wall of the bladder with the tumor can be sucked by vacuum, and only local chemotherapy of the tumor can be performed without affecting health tissues.

The inventive method protects other organs and tissues of a patient's body from substances used in chemotherapy.

It will be understood that each of the elements described above, or two or more together, may also find a useful application in other types of constructions differing from the types described above.

While the invention has been illustrated and described as embodied in method of and device for destroying foreign formations in a body, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A method of destroying formation in a body, comprising the steps of introducing a tubular member into a body to an area of a formation with gripping means provided at a front end of the tubular member and having a plurality of gripping elements which are movable between an open position in which said gripping elements are spaced from one another around an axis of the tubular member and a closed position in which said gripping elements are located close to one without gaps therebetween to enclose a substantially closed space; moving a tube inside the tubular member axially in a first axial direction so that the griping elements connected to the tubular member and to the tube are displaced to their open position to surround a formation, and then moving the tube in an opposite axial direction so that the gripping elements are moved to their closed position and form a substantially closed space to confine the formation inside the closed space; destroying the formation by a formation destroying element which is introduced through an interior of the tube and therefore into an interior of the tubular member with a working head brought in contact with the formation and rotatable to destroy the formation; withdrawing a device from a body with the formation and its fragments confined inside the closed space formed by the gripping elements in their closed position.

2. A method as defined in claim 1; and further comprising illuminating an area of the formation and viewing the areas through an eyepiece and a light guide extending from the eyepiece through the tubular member.

3. A method as defined in claim 1; and further comprising forming the gripping elements of the tubular member as hinge tongs.

4. A method as defined in claim 1; and further comprising forming the gripping elements of the tubular member as spring tongs.

5. A method as defined in claim 1; and further comprising forming said degripping elements and moving them so that their lateral edges are in contact with one another so as to form a completely closed space to confine the formation.

6. A method as defined in claim 1; and further comprising forming and moving said gripping elements so that their lateral edges are located close with one another with smallest possible gaps to provide the substantially closed space to confine the formation inside the closed space.

7. A method as defined in claim 1; and further comprising placing a cap on at least a front end of the gripping element so as to provide the substantially closed space to confine the formation.

8. A method as defined in claim 1; and further comprising making the cap of a flexible material for allowing fitting the cap on said gripping elements.

9. A method as defined in claim 1; and further comprising providing turning of the tube by the electric motor connected with the tube.

10. A method as defined in claim 1; and further comprising displacing the tube in a longitudinal direction by an element which can be switched on and off by a right hand and a left hand of the user.

* * * * *